United States Patent [19]

Pulverer

[11] Patent Number: 4,647,456

[45] Date of Patent: Mar. 3, 1987

[54] METHODS OF INCREASING TOLERANCE TO RADIOTHERAPY AND CHEMOTHERAPY USING PROPIONI BACTERIA

[75] Inventor: Gerhard Pulverer, Cologne, Fed. Rep. of Germany

[73] Assignee: Dr. Madaus & Co., Cologne, Fed. Rep. of Germany

[21] Appl. No.: 688,278

[22] Filed: Jan. 3, 1985

Related U.S. Application Data

[63] Continuation of Ser. No. 304,485, Sep. 22, 1981, abandoned.

[51] Int. Cl.⁴ .............................................. A61K 35/74
[52] U.S. Cl. ....................................... 424/95; 424/92; 424/195.1; 378/65
[58] Field of Search ...................... 424/92, 195, 195.1, 424/95; 378/65

[56] References Cited

PUBLICATIONS

Saino et al.–Chem. Abst., vol. 85 (1976), p. 2259v.
Szmigielski et al–Zentralbl. Bacteriol, vol. 248, No. 3 (1980), pp. 286–295.
Roszkowski et al–Med.Mikrobiol Infektionskr Parasitol, vol. 246, No. 3 (1980), pp. 393–404.
Azuma et al–Chem. Abst., vol. 86 (1977), p. 3460m.

*Primary Examiner*—Sam Rosen
*Attorney, Agent, or Firm*—Felfe & Lynch

[57] ABSTRACT

It has been found that compositions derived from Propioni bacteria, especially *P. granulosum, P. avidium*, and *P. acnes* are useful in increasing tolerance of individuals to radiotherapy and chemotherapy. When these compositions are administered before or during a regimen of radio- or chemotherapy, the subject can receive higher doses of radiation and chemicals without harmful side effects.

6 Claims, 1 Drawing Figure

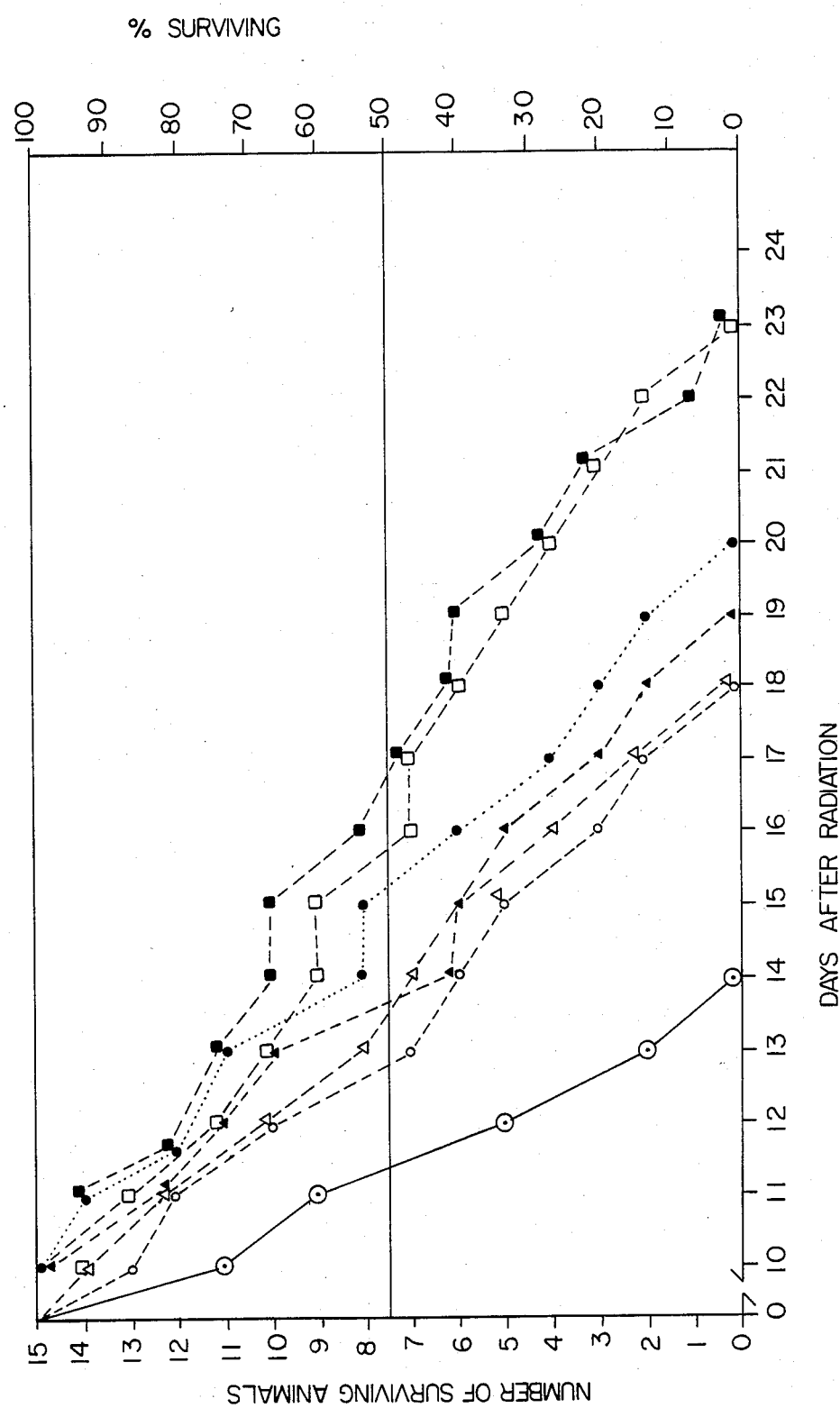

METHODS OF INCREASING TOLERANCE TO RADIOTHERAPY AND CHEMOTHERAPY USING PROPIONI BACTERIA

This application is a continuation of application Ser. No. 304,485, filed Sept. 22, 1981, now abandoned.

The present invention relates to the use of Propioni bacteria. It relates, especially, to the use of *Propioni bacterium granulosum, Propioni bacterium avidum,* and/or *Propioni bacterium acnes* for the manufacture of cell-wall preparations or whole-cell preparations that are useful in tumor treatment, as well as in radiotherapy or chemotherapy of tumors.

Preparations of anerobic Coryneforms, for example, *C. parvum,* CN 6134, which have been described as antitumor agents, are familiar. It has turned out, however, that in systematic or local therapy, these preparations lead to undesirable side-effects and complications, so that it is recommended in the literature that doses of more than 7.5 mg/m² of surface be avoided. This quantity would correspond approximately to a quantity of 20 mg per patient.

According to the present invention, it was established that preparations based on killed whole cells or cell walls from Propioni bacteria are extraordinarily effective in the chemotherapy or adiotherapy of tumors. These preparations, in particular, are suitable for supportive therapy. The effect is especially great with local administration.

Thus, it has been shown by experimentation that *P. acnes, P. granulosum,* and *P. avidum,* with intraperitoneal injection in mice of a dose of 1.5 mg per mouse, significantly prolong the survival period of mice that have been subjected to lethal radiation (850 R), *P. granulosum* being the most effective. It was established that the preparations according to the present invention are suitable for stimulation of CFU-S proliferation, that is, stimulation of a migration of hemopoietic colony-forming units from the bone marrow to entry into the cell cycle and to migration to the peripheral blood. In clinical practice, this finding means that the preparations according to the present invention are valuable as supportive therapy in the radiotherapy of tumors, since they substantially increase the tolerance of the patients to radiation.

In addition, it was established by investigations that the preparations according to the present invention were effective against murine sarcoma 180 in mice, and led to a regression of more than 70% of the sarcoma 180 tumors, when applied intratumorally.

It was also established that the preparations according to the present invention, when administered systemically to patients with primary or secondary lung tumors as a supplementary treatment with chemotherapy, help to avoid one of the chief complications in the chemotherapy of tumors, namely, the danger of infections. Thus, it appears that the preparations according to the present invention may be used as excellent supplementary agents, with an antibacterial effect, in the chemotherapy of cancer.

The foregoing results, which are proved by statements on some in vivo experiments below, must be evaluated as unexpected in every respect.

The use according to the present invention for the manufacture of cell-wall preparations has proved to be especially useful, since, with this type of preparations, the danger of undesireable side-effects is particularly slight. Cell wall preparations have not been previously investigated clinically according to the state of the art.

The subject of the present invention is, thus, the use of *Propioni bacterium granulosum, Propioni bacterium avidum* and/or *Propioni bacterium acnes* for the manufacture of cell-wall preparations or whole-cell preparations in radiotherapy or chemotherapy of tumors.

According to a preferred form of carrying out the present invention, *Propioni bacterium granulosum, Propioni bacterium avidum,* particularly *Propioni bacterium granulosum,* Strain KP 45, and *Propioni bacterium avidum,* Strain KP 40, are used.

It is preferable to manufacture injectable suspension in phosphate-buffered salt solution. In so doing, a concentration of 0.5 to 50 mg of active material per ml of solution in particularly expedient. A concentration of 2 to 12 mg/ml of solution, particularly of 5 to 7.5 mg/ml of solution is preferred.

Especially suitable are intravenous infusion solutions containing 15 to 30 mg of the preparation in 100 ml of solution. Such as dosage quantity has proved to be especially advantageous in administration in the treatment of primary and secondary lung neoplasms, when a first injection should take place at least 10 days before chemotherapeutic treatment.

It is expedient to use $Na_2HPO_4/KH_2PO_4$ phosphate buffer that has a pH of about 7.2 as a phosphate buffer.

The present invention is not limited to a special Propioni bacterium strain. Various Propioni bacteria strains come under consideration ; for example, the Propioni bacteria described in *FEMS Microbiology Letters,* Vol. 2, No. 1 (July 1977), pp. 5–9.

The strains *P. granulosum* KP 45 and *P. avidum* KP 40 are especially preferred. They were filed with the DSM (Deutsche Sammlung von Mikroorganismen, Gesellschaft für Biotechnologische Forschung mbH [German Collection of Microorganisms, Society for Biotechnological Research, Ltd.], Grisebachstrasse 8, D-3400 Göttingen, West Germany), with DSM Receiving numbers 1773 for P. granulosum KP 45 and 1772 for P. avidum KP 40, with Mar. 11, 1980 as the date of receipt. Both strains are available at the DSM, in conformity with the release document (at present, Form 2750), which is to be presented by the filer at the DSM and the German Patent Office.

*P. granulosum, P. acnes,* and *P. avidum* can, besides, be isolated and grown from smears of acne efflorescences (*acne vulgaris, acne papulopustulosa,* and *acnes conclobata*). For taxonomy, cf. *Der Hautarzt,* 30 (1979), pp. 242–267.

Additional Propioni bacteria strains that come under consideration for use according to the present invention have, for example, been described in *Applied Microbiology,* Vol. 25, No. 2 (February 1973), pp. 222–229, of the American Society for Microbiology.

The following examples serve to explain the manufacture of preparations according to the present invention.

BRIEF DESCRIPTION OF THE FIGURE

The FIGURE shows the influence of Propioni Bacteria on the Survival of Mice what have been subjected to lethal radiation (850 R).

| | |
|---|---|
|  | P. granulosum (whole cells)<br>P. granulosum (cell walls)<br>P. acnes (whole cells) |

-continued

| | |
|---|---|
| ●—● | P. acnes (cell walls) |
| △---△ | P. avidum (whole cells) |
| ▲---▲ | P. avidum (cell walls) |
| ⊙---⊙ | untreated control |

EXAMPLE 1

General Procedure for Obtaining Cell Walls

The liquid culture of the particular Propioni bacterium took place in 1 liter (Erlenmeyer flask) at 37° C. under anerobic conditions (Gas-Pak Process, BBL).

For this mass culture, the medium (A-bouillon* or Triptic soy broth, Difco) was inoculated with a thick suspension of Propioni bacterium. The suspension for the inoculation was prepared by triturating a three-day A agar culture of Propioni bacterium in 10 ml of bouillon. After an incubation period of 72 hours at 37° C., the cells were separated from the liquid by centrifuging at 10,000 g (20 min) in a Sorval R2 cooling centrifuge. The sediment was washed three times with distilled water, and then mixed with the double the volume of glass beads (φ0.17–0.18 mm), and crushed in a cell mill* for 1 to 1½ hours. After a test had been carried out by microscopic examination (Gram's preparation) to check that no whole cells were present anymore, the glass beads were separated from the homogenizate by using phosphate buffer (pH 7.2) with a G-1 frit.
*A-bouillon

| | |
|---|---|
| Bacto Casitone | 12 g |
| Bacto yeast extract | 12 g |
| KH$_2$PO$_4$ | 4 g |
| MgSO$_4$·7H$_2$O | 1 g |
| glucose | 4 g | distilled water to make up 1,000 ml, pH 7.2 for A agar +28 g of Bacto agar.
**phosphate buffer: 1/15 M Na$_2$HPO$_4$.2H$_2$O and 1/15 M KH$_2$PO$_4$ were each dissolved in 1,000 ml of distilled water; 612 g of the secondary sodium phosphate solution was mixed with 388 G of the primary potassium phosphate solution, and the pH was adjusted to 7.2.
***cell mill: Vibrogen Zellmühle vi 3, Edmund B/ühler, 7400 Tübingen.

The milky suspension (containing cell walls and cytoplasm) was centrifuged off for 20 min at 40,000 g, and the sediment was taken up in phosphate buffer (pH 7.2). The autolytic enzymes were inactivated by boiling 10 min on a water bath.

These cell walls, which still contained protein, were further purified by incubation with trypsin (Merck, 0.5 ml/ml of suspension) at 37° C. for 24 hours and 1 ml of toluene to 100 ml of suspension (to prevent bacterial growth).

The cell walls that had been purified by digestion with trypsin were finally centrifuged off (30 min), washed 3 times with distilled water, and then freeze-dried.

EXAMPLE 2

Characterization of the Propioni Bacteria
P. avidum Strain KP40 und P. granulosum KP45

| Strain No. | Origin | Species | Biochemical Reactions (Lit. 1) | | | | | | | | | |
|---|---|---|---|---|---|---|---|---|---|---|---|---|
| | | | Saccharose | Maltose | Sorbite | Mannite | Salicin | Inosite | Esculin Hydrolysis | Indole | Nitrate | Gelatin |
| KP45 | Smear from a wound infection | P. granulosum | + | + | − | − | − | − | − | − | − | − |
| KP40 | Taken from preputial area of a clinically healthy patient | P. avidum | + | + | − | + | + | − | ++ | − | − | + |

| Strain No. | Origin | Species | Biochemical Reactions (Lit. 1) | | Seriology (Lit. 2) | | | | | | Type of phagocytolysis (Lit. 3) |
|---|---|---|---|---|---|---|---|---|---|---|---|
| | | | Dextrin | Melizitose | P. acnes KB | P. granulosum 95 | D34 | P. avidum 58 | 0575 | 31 | Ko1 ... K013 |
| KP45 | Smear from a wound infection | P. granulosum | + | + | − | + | − | − | − | − | NT |
| KP40 | Taken from preputial area of a clinically healthy patient | P. avidum | + | + | − | − | − | + | − | − | NT |

NT = can not be typed
(1) G. Pulverer and H. L. Ko Fermentative and Serological Studies on *Propionibacterium acnes* and App. Microb. 25 : 222–229 : 1973
(2) U. Hoffler, H. L. Ko and G. Pulverer Serotyping of *Propionibacterium acnes* and related microbial species. Fems Microbiology letters, Vol. 2; 5–9, 1977
(3) E. C. Jong, H. L. Ko and G. Pulverer Studies on Bacteriophanges of *P. acnes* Med. Microbiol. Immunol. 161, 263–271, 1975
Der Hautarzt 30, 242–247 (1979) Differenzierung unterschiedlicher Propionibakterienspezie aus *Acne-vulgaris*-Effluoreszenzen [Differentiation of Various Propioni Bacteria Species from *Acne vulgaris* Efflorescences]

Preparation of Suspensions of P. acnes (Strain ATCC 6919, P. avidum (Strain 0575, KP 40) and P. granulosum (Strain KP 45)

According to the general procedure in Example 1, lyophilized Propioni bacteria of the type mentioned are suspended in phosphate-buffered salt solution of the type mentioned above, in a concentration of 5.0 or 7.5 mg/ml. The suspension obtained in suitable, especially, for intraperitoneal injection.

EXAMPLE 3

Using the procedure of Example 3, suspensions that can be injected intraperitoneally are prepared from P. granulosum, Strain KP 45, 95 K, P. acnes, Strain ATCC 6919, and P. avidum, Strain 0575, KP 40, from lyophilized material, with a concentration of 5 or 7.5 mg/ml of cell material.

EXAMPLE 4

Preparation of Injectable Suspensions for Supplementary Treatment in Chemotherapy

*P. granulosum*, Strain KP 45, is prepared according to the general procedure of Example 1. A suspension is made of 30 mg of cell material in 100 ml of infusion solution for intravenous administration.

The preparations according to the present invention may contain customary fillers. The preparations may be available in ampoule form or they maby be put into sterile bottles with seals that can be pierced. Forms that can be manufactured with separate storage of the components, for preparation at the moment of application, also come under consideration.

In vivo Investigations

1. Hemopoiesis in Mice Treated with Propioni Bacteria after Lethal Radiation

Three strains of Propioni bacteria (*P. acnes P. granulosum*, and *P. avidum*) were injected intraperitoneally in mice that had been subjected to lethal radiation (850 (R), in a dosage, in each case, of 1.5 mg per mouse. In so doing, it turned out that P. granulosum prolonged the survival period of the mice that had been subjected to radiation the most.

Adult, eight-week-old male Swiss mice were used. The animals were fed a standard diet. Water was freely available. The water and food were sterilized. The water contained oxytetracycline (1 g per 1,000 ml).

Radiation

The mice were subjected to radiation of 650 or 850 R in a rotating metacrylate cage (10 mice per cage), at a distance of 50 cm from the THX 250 Medicor unit, which was operated at 200 kV and provided with a 0.5 mm Cu filter. The radiation rate of about 75 R per minute was determined with a CT-1 thermoluminescence R-dosimeter.

*P. acnes*, Strain ATCC 6919, *P. avidum*, Strain 0575, KP 40, and *P. granulosum*, Strain KP 45, were used for the experiments in the form of killed whole cells and in the form of cell walls. The lyophilized Propioni bacteria were suspended in a phosphate-buffered salt solution in a concentration of 7.5 mg/ml, and 0.2 ml of the suspension was injected intraperitoneally (1.5 mg per mouse).

Investigation of Exogenous Spleen Colonies 3, 2, or 1 day before the transplant of bone marrow, the donor mice were injected with 1.5 mg of *P. granulosum*. The bone-marrow-cell suspension was prepared by washing both thigh bones with sterile Parker medium. The cells were counted in a hemocytometer. $5 \times 10^5$ cells that were capable of reproduction in 0.2 ml of Parker medium were injected into the tail vein of each mouse, which had been subjected to radiation of 850 R 4 hours before the bone marrow transplant. 0.2 ml of medium or $5 \times 10^5$ bone marrow cells from normal the control mice. *P. granulosum* was administered, as before to another group of donor mice; then the animals were anesthetized with ether, and blood was removed from the retrobulbar plexus. The blood cells were counted in a hemocytometer, and aliquot portions of blood with $5 \times 10^5$ nucleated cells were injected into the tail veins of mice that had been subjected to radiation of 850 R. The control mice received equal volumes of blood that had been taken from normal mice (not treated with *P. granulosum*). All the mice were killed and weighed 9 days after the transplant of blood or bone marrow, the spleen was removed, weighing was carried out again, and the number of colonies per spleen was determined after fixing in chloroform:ethanol (1:3).

Investigation of Endogenous Spleen Colonies 3, 2 or 1, or 0 days before being subjected to radiation of 650 R, mice were injected intraperitoneally with *P. granulosum*. The control mice received the same volumes of PBS (phosphate-buffered salt solution). 9 days after being subjected to radiation, the animals were killed, the spleens were removed, weighed, and the colonies were counted, as in the above test, to determine the exogenous spleen colonies.

Survival Test

Mice were divided into 7 groups, with 15 mice per group in each case, and were subjected to x-ray radiation of 850 R. 4 hours after being subjected to radiation, cell walls or whole cells of Propioni bacteria were injected into the animals. The control mice received the same volumes of PBS. From the 10th day after radiation on, the number of surviving animals in each group was counted.

The Student t-test was used for the statistical analysis.

The effect of the Propioni bacteria that were investigated on the survival rate of the mice had been subjected to lethal radiation is presented in graphic form in the attached FIG. 1. In comparison with the control animals, all three strains of Propioni bacteria led to a significant prolongation of the survival span. *P. granulosum*, in the form of the whole cell preparation and in the form of the cell-wall preparation, proved to be more effective than *P. acnes* and *P. avidum*.

The Influence of P. granulosum on Endogenous Spleen Colonies (Strain KP 45)

TABLE I

The Number of Endogenous Spleen Colonies in Mice That Were Treated with *Propioni bacterium granulosum* (Strain KP 45)
(Average Value ± Standard Deviation)

|  | relative weight of spleen | number of endogenous spleen colonies |
|---|---|---|
| Control/650 R/ | 1.82 ± 0.45 | 1.24 ± 0.67 |
| P. granulosum - 3 days before radiation | 1.66 ± 0.24 | 10.6 ± 4.45$^x$ |
| P. granulosum - 2 days before radiation | 1.73 ± 0.21 | 8.17 ± 3.49$^x$ |
| P. granulosum - 1 day before radiation | 2.18 ± 0.42 | 11.2 ± 5.30$^x$ |
| P. granulosum - 4 hours after radiation | 2.32 ± 0.38 | 14.1 ± 4.70$^x$ |

$^x$ - p <0.01

The relative weight of the spleens of the mice that were subjected to radiation only increased if P. granulosum was administered 1 day before or 4 hours after radiation with 650 R. The number of exogenous spleen colonies in all treatments, however, increased significantly.

The Effect of P. granulosum on the Formation of Exogenous Spleen Colonies (Strain KP 45)

No differences were established in the relative weight of the spleen between mice that had received normal bone-marrow transplants and mice that had received bone marrow from donor animals that had been treated with P. granulosum 2, 3, or 1 days before the transplant.

TABLE II

Number of Exogenous Colonies after Transfusion of Bone Marrow from Mice Treated with P. granulosum (Strain KP 45) (Average Values ± Standard Deviations)

| Transfusion | Relative weight of spleen | Number of exogenous spleen colonies | CFU-S per $10^6$ nucleated bone marrow cells |
|---|---|---|---|
| Control (0.5 ml of Parker medium) | 0.99 ± 0.19 | 1.12 ± 0.32 | 11.2 ± 3.2 |
| Bone marrow from normal mice | 1.52 ± 0.31 | 20.4 ± 2.14 | 204.0 ± 21.4 |
| Bone marrow from mice that had been treated with P. granulosum 3 days before the transfusion | 1.51 ± 0.49 | $10.3 ± 1.87^x$ | $103.0 ± 18.7^x$ |
| Bone marrow from mice that had been treated with P. granulosum 2 days before the transfusion | 1.75 ± 0.44 | $11.6 ± 4.4^x$ | $116.0 ± 44.2^x$ |
| Bone marrow from mice that had been treated with P. granulosum 1 day before the transfusion | 1.69 ± 0.27 | $10.7 ± 4.3^x$ | $107.0 ± 43.3^x$ |

$^x$- p 0.01

This treatment led to a significant decrease in the number of exogenous spleen colonies in animals that had been subjected to radiation of 850 R, in comparison with animals to whom the bone marrow of untreated donor animals had been given. This finding shows a decrease in the number of CFU-S in the bone marrow of mice that were treated with P. granulosum. On the other hand, an injection of blood from mice that had been treated with P. granulosum in experimental animals that had been subjected to lethal radiation led to a significant increase in the values of the relative spleen weights and the number of spleen colonies, in comparison with the injection of blood from untreated donor animals, as can be understood from Table III below:

proliferative ability of the hemopoietic parent cells and of the damage to the epithelial cells of the inner organs, with subsequent development of generalized infections by saprophytic bacteria. It is evident from the above experiment, of course, that the mice treated with Propioni bacteria do not exhibit any symptoms of diarrhea and/or hemorrhages from the digestive tract. The protective effect of the Propioni bacteria, therefore, can be ascribed to the increased recovery of the hemopoietic parent cells of the bone marrow after the radiation.

2. The Effectivness of P. granulosum, P. acnes, and P. avidum in Experimetal murine Sarcoma 180-Tumor in Mice All three previously mentioned Propioni bacteria were administered intraperitoneally or intratumorally in several doses of 1 mg per mouse, in each case, and proved to be effective in retarding the growth and stimulating the regression of sarcoma 180 in CFW-mice. In addition, the use of Propioni bacteria resulted in the prolongation of the survival of mice with sarcoma 180.

The Propioni Bacteria Used

Propioni bacterium KP 45 (isolated from a wound

TABLE III

Number of Exogenous Spleen Colonies after Transfusion of Blood from Mice Treated with P. granulosum (Strain KP 45) (Average Values ± Standard Deviations)

| Transfusion | Leucocytosis with the transfused blood | Relative weight of spleens | Number of exogenous spleen colonies | CFU-S per $10^6$ nucleated ated bone marrow cells |
|---|---|---|---|---|
| Blood from normal mice | 6480 | 1.41 ± 0.23 | 3.8 ± 2.2 | 1.17 ± 0.28 |
| Blood from mice that had been treated with P. granulosum 3 days before the transfusion | 9960 | $2.62 ± 0.88^x$ | $9.16 ± 1.4^x$ | $1.84 ± 0.31^x$ |
| Blood from mice that had been treated with P. granulosum 2 days before the transfusion | 10120 | $3.45 ± 1.81^x$ | $10.2 ± 2.6^x$ | $2.01 ± 0.34^x$ |
| Blood from mice that had been treated with P. granulosum 1 days before the transfusion | 9650 | $3.23 ± 1.48^x$ | $7.4 ± 1.8xx$ | $1.54 ± 0.23xx$ |

$^x$- p < 0.01
$^{xx}$- p < 0.05

Blood that had bee taken from donor mice which had been injected with P. granulosum two or three days before the blood transplant was most effective in stimulating the formation of spleen colonies. Leucocytosis in transplanted blood was increased, however, after treatment with P. granulosum 3, 2, or 1 day before the blood was taken.

In the experiments above, P. granulosum proved itself to be the most effective agent in rats that had been subjected to lethal radiation. The fatal effect of the lethal dose of x-rays is the result of the inhibiting of the infection in the Hygiene Institut of the University of Cologne), Propioni bacterium acnes, Strain 6919 (ATCC), Propioni bacterium avidum, Strain 0575 (C. S. Cummins, Anaerobe Labs, Virginia Polytechnic Inst. and State University, Blacksburg), KP 40 were used for the experiments. The Propioni bacteria mentioned were lyophilized, and suspended in a phosphate-buffered salt solution in a concentration of 5 mg/ml. 0.2 ml of the suspension was administered intraperitoneally or intratumorally to the mice that had tumors.

The Mice Having Tumors

With this tumor system, adult male CFW mice were used. The tumors were induced as described in *Radio Sci.*, 12 (1978), pp. 185-189. For this purpose, sarcoma 180-tumors from donor mice were dissected, tumor tissue was minced up, trypsinized (0.25% trypsin, 15 minutes at 37° C.), and filtered. The number of cells was counted and adjusted to $10^8$ cells capable of reproduction per 1 ml of salt solution. 0.1 ml of the suspension was injected subcutaneously and intrascapularly. This procedure led to the development of palpable tumors after about 4 to 5 days. Rapid growth of the tumors took place between the 4th and the 14th day after the transplant, with the lethal effect appearing between the 20th and 28th day.

A total of 225 male CFW-mice were used in the investigations. In the survival tests, 105 mice were divided up into seven groups (15 mice in each group), and the animals of the experimental groups (I TO VI) were injected with Propioni bacteria on days 0, 4, 8, 12, and 16 after the implantation of the tumor cells. *P. granulsoum, P. avidum,* or *P. acnes* was injected intraperitoneally (3 groups) or intratumorally (3 groups) in a dosage of 1 mg/mouse. The control mice received intraperitoneal or intratumoral injections of PBS. The number of surviving animals was recorded on the 16th or 20th day after implantation of the tumor cells and then every second day up to the 44th day after the implantation. The remaining 120 animals were divided up into 8 groups. Mice of the experimental groups (I to VI) were injected with Propioni bacteria, as before, and the control mice (groups VII and VIII) were injected with PBS. On the 20th day after the implantation of the tumor cells, all the mice were killed, and the tumors were dissected and weighed. The arithmetical average and the standard deviations were determined for each group. All the tumors of the experimental groups that were more than two standard deviations below the average value for the control were recorded as regressive. The results were analyzed statistically by means of the Student t-Test (tumor mass) or the Chi-Square-Analysis with Yates Correction (regression of the tumors and survival of the mice).

The results achieved are summarized in Table IV below.

TABLE IV
Survival of CFW-Mice Having Sarcoma 180, under Treatment with Propioni Bacteria (1 mg/Mouse) on Days 0, 4, 8, 12, and 16 after the Implantation of Tumor Cells

| | Days after the Implantation of the Tumor Cells | | | | | | | | | | | | | |
|---|---|---|---|---|---|---|---|---|---|---|---|---|---|---|
| | 16 | 20 | 22 | 24 | 26 | 28 | 30 | 32 | 34 | 36 | 38 | 40 | 42 | 44 |
| Control | 15 | 13 | 10 | 7 | 3 | 0 | | | | | | | | |
| P. granulosum intraperitoneal | 15 | 15 | 15 | 15 | 12 | 12 | 10 | 9 | 9 | 7 | 6 | 5 | 3 | 3 |
| P. acnes intraperitoneal | 15 | 15 | 15 | 15 | 15 | 14 | 12 | 8 | 8 | 8 | 5 | 5 | 2 | 1 |
| P. avidum intraperitoneal | 15 | 15 | 15 | 14 | 14 | 13 | 11 | 10 | 8 | 5 | 4 | 4 | 0 | |
| P. granulosum intratumoral | 15 | 15 | 15 | 15 | 15 | 15 | 13 | 12 | 11 | 9 | 7 | 7 | 6 | 3 |
| P. acnes intratumoral | 15 | 15 | 15 | 15 | 15 | 14 | 12 | 11 | 9 | 7 | 7 | 7 | 5 | 2 |
| P. avidum intratumoral | 15 | 15 | 15 | 15 | 15 | 15 | 14 | 13 | 10 | 8 | 8 | 6 | 4 | 3 |

Table V below shows the influence of Propioni bacteria on the growth and regression of sarcoma 180 in CFW mice.

TABLE V
Tumor Mass and Number of Regressed Tumors in Mice Having Sarcoma 180 Which Were Treated with Propioni Bacteria (1 mg/mouse) on the 0, 4th, 8th, 12th, and 16th Day after Implantation of Tumor Cells

| | Intraperitoneal Injection | | | Intratumoral Injection | | |
|---|---|---|---|---|---|---|
| | Tumor Mass (g) | Number of regressed tumors | Percentage of regression | Tumor Mass (g) | Number of regressed tumors | Percentage of regression |
| Control | 2631 ± 321 | 0/15 | 0 | 2631 ± 321 | 0/15 | 0 |
| Propioni bacterium granulosum | 842 ± 312 | 8/15 | 53.3 | 538 ± 212 | 11/15 | 73.3 |
| Propioni bacterium avidum | 1032 ± 381 | 6/15 | 40.0 | 842 ± 246 | 10/15 | 66.6 |
| Propioni bacterium acnes | 1126 ± 412 | 5/15 | 33.3 | 731 ± 218 | 9/15 | 60.0 |

With intraperitoneal administration in a single dose of 1 mg/mouse, there was a significant enlargement of the spleen on the 4th day after the injection, with further enlargement of the spleen mass on days 6 to 14, in all three strains of Propioni bacteria that were tested. This enlargement of the spleen reflects the stimulation of the reticuloendothelial system, and runs parallel to the antitumor activity of these immunostimulators.

*P. granulosum* led to a regression of more than 70% in the sarcoma 180-tumors that were investigated, if it had been administered intratumorally.

3. In vivo Cytostatic Effectiveness in Murine Tumor Cells by *Propioni bacterium granulosum*

In a further investigation, the cytostatic effect of *Propioni bacterium granulosum*, Strain KP 45, in sarcoma L-1 in BALB/c mice (lung) was investigated. Here, too, there was significant effectiveness in comparison with untreated animals.

4. Antibacterial Effect as a Supplementary Treatment in the Chemotherapy of Primary or Secondary Lung Tumors For this test, 30 patients with primary or secondary metastatic lung tumors were selected. 10 of the patients received intravenous infusions of 30 mg of *P. granulosum* in 100 ml of intravenous infusion solution. The other 20 patients served as a control.

All the patients were treated chemotherapeutically to synchronize the proliferation of neoplastic cells. Each course lasted 3 days: 1st day: 1.5 mg of vincristine intravenously at 8 a.m. and at 8 p.m., 2nd day 25 mg of methotrexate intramuscularly at 8 p.m., 3rd day: 25 mg of methotrexate intramuscularly at 8 a.m., followed by 25 mg of methotrexate intravenously at 2 p.m. and an infusion of 30 mg/kg of cyclophosphamide at the same time.

This chemotherapeutic treatment was repeated three times every 21 days.

The total chemotherapy consisted of the three cycles above, which began, in each case, on the 1st, 22nd, and 43rd day of observation.

During the 3rd, 10th, 31st, and 52nd day of observation, P. granulosum was administered in a dose of 30 mg/100 ml of intravenous infusion solution in the course of 15 minutes (on the last day of the first chemotherapeutic cycle, and then 1 week after the end of each cycle).

In the patients that were treated only therapeutically, five cases of bacterial infection appeared (three pneumonias, one sepsis, and one case of angina tonsillaris) during a 60-day period of observation, while in the 10 patients treated with chemotherapy and intravenous infusions of *P. granulosum*, no symptoms of bacterial infection appeared. This difference should be designated as statistically significant.

The tolerance of the patients to intravenous infusions of *P. granulosum*, Strain KP 45, was good. During the infusion, in an amount of 30 mg of *P. granulosum*, chills and then fever up to 102.2° F. did, indeed, appear; on the following day, however, these side-effects could no longer be observed. Repeated infusions of *P. granulosum* did not lead to the development of a delayed hypersensitivity during the 60-day observation. From this, it is concluded that the intravenous infusion of 30 to 240 mg of *P. granulosum*, Strain KP 45, can be undertaken without the risk of serious side-effects or complications in patients.

5. General Directions for Local Administration (Cancer of the Stomach and Intestine)

10 mg of lyophilized product is suspended in 1 ml of 1% xylocaine in salt solution and injected intratumorally through the skin (diameter 1 mm), for which an 80 cm-long, stiff polyethylene tube with a firmly attached intramuscular needle (18 gauge) without an epiphysis. The tube is introduced by means of a biopsy cannula in an endoscope (gastrofiberscope or colonoscoop, and the neoplastic tumor, which is under visual control, is punctured, and the needle is introduced 0.5 to 1 cm into the tumor tissue. The product is injected through the tube, and washing is carried out with 1 to 2 ml of 1% xylocaine in salt solution.

The intratumoral injections (10 mg of product in each case) are administered, for example, during the first three days, thenon the 10th and on the 17th day of observation.

What is claimed is:

1. A method of increasing a person's tolerance to radiotherapy or chemotherapy comprising administering to said person during a regimen of said radiotherapy or chemotherapy an effective amount of a pharmaceutical composition comprising *Propioni bacterium avidium*, strain KP40 and/or Propioni bacterium strain KP45 cell walls or whole cell preparations.

2. Method of claim 1, wherein said composition is administered by injection intravenously, intraperitoneally, or intratumorally.

3. A method as in claim 1, wherein said composition is administered to a subject with cancer.

4. A method as in claim 3, wherein said cancer is selected from the group consisting of stomach, intestinal, or lung cancer.

5. A method of increasing a person's tolerance to radiotherapy radiation comprising administering to said person during a regimen of said radiotherapy an effective amount of a composition comprising *Propioni bacterium avidium* strain KP45 cell wall or whole cell preparation.

6. A method as in claim 5, wherein said composition is administered by injection intravenously, intraperitoneally, or intratumorally.

* * * * *